US007655700B2

(12) United States Patent
Jordan et al.

(10) Patent No.: US 7,655,700 B2
(45) Date of Patent: Feb. 2, 2010

(54) TRANSGENIC MOUSE MODEL AND METHODS FOR TREATMENT OF NEURO MUSCULAR DISEASE BY INTERFERING WITH ANDROGEN-ANDROGEN RECEPTOR INTERACTION IN SKELETAL MUSCLES

(75) Inventors: Cynthia Jordan, East Lansing, MI (US); Douglas A. Monks, Toronto (CA); Marc Breedlove, East Lansing, MI (US)

(73) Assignee: Michigan State University, East Lansing, MI (US)

( * ) Notice: Subject to any disclaimer, the term of this patent is extended or adjusted under 35 U.S.C. 154(b) by 29 days.

(21) Appl. No.: 11/509,455

(22) Filed: Aug. 24, 2006

(65) Prior Publication Data

US 2007/0061909 A1    Mar. 15, 2007

Related U.S. Application Data

(60) Provisional application No. 60/711,333, filed on Aug. 25, 2005.

(51) Int. Cl.
  *A01N 37/18*  (2006.01)
  *A01N 43/80*  (2006.01)
  *A01N 43/56*  (2006.01)
  *C12Q 1/68*  (2006.01)
  *A01K 67/00*  (2006.01)
  *A01K 67/027*  (2006.01)
  *C12N 15/00*  (2006.01)
(52) U.S. Cl. ................ 514/629; 514/379; 514/406; 435/6; 800/8; 800/18; 800/21
(58) Field of Classification Search .............. None
See application file for complete search history.

(56) References Cited

U.S. PATENT DOCUMENTS

| 2003/0049627 | A1 | 3/2003 | Nguyen et al. |
| 2004/0087557 | A1 | 5/2004 | Steiner et al. |

FOREIGN PATENT DOCUMENTS

| EP | 0703228 B1 | 3/2002 |
| EP | 0703231 B1 | 5/2002 |
| EP | 0806420 B1 | 8/2002 |
| EP | 0651993 B1 | 10/2002 |
| EP | 0747377 B1 | 8/2003 |
| EP | 1255113 B1 | 5/2004 |
| WO | 03/078463 A1 | 9/2003 |

OTHER PUBLICATIONS

Katsuno et al., 2003, Nature Medicine. 9:768-773.*
Fishman et al., Brain. Res. Dev. Brain Res. 70:283-286.*
Darrington et al., 2002, Molecular Neurosci. 13:2117-2120.*
Garofalo et al.,1993, Neuromuscul. Disord. 3:195-199.*
Cyproterone_dm.pdf. (http://www.cancercare.ns.ca/documents/Cyproterone_dm.pdf, by Cancer Care Nova Scotia, 2003).*
Flutamide_BC Cancer Agency.pdf. (http://www.bccancer.bc.ca/HPI/DrugDatabase/DrugIndexPro/Flutamide.htm. by BC Cancer Agency, 2007).*
Greenland et al., 2004, Int. Med. J. 34-279-286.*
Balthazart et al, "Sexual differences in the Japanese quail: behavior, morphology, and intracellular metabolism of testosterone," Gen Comp Endocrinol, vol. 51 (No. 2), p. 191-207/Abstract, (Aug. 1983).
Bingham et al, "Transgenic mice expressing and androgen receptor gene with an expanded CAG repeat in skeletal muscle," American Journal of Human Genetics, vol. 57 (No. 4), p. A326, (1995).
Marron et al, "Androgen-induced neurite outgrowth is mediated by neuritin in motor neurones," Journal of Neurochemistry, vol. 92, p. 10-20, (Jan. 2005).
Monks et al, "Increased androgen receptor expression in skeletal muscle fibers induces androgen-androgen dependent muscle pathology," Society of Neuroscience Annual Meeting/Abstract, (Aug. 27, 2004).
Nakajima H, et al, "Tissue variability of androgen receptor gene in bulbospinal muscular atrophy-comparison of the number of CAG repeats between muscles and peripheral blood leukocytes," Rinsho Shinkeigaku, vol. 33 (No. 10), p. 1103-1105, (Oct. 1993).
Simon et al, "Increased androgen receptor expression in skeletal muscle fibers leads to muscle pathology,"Society of Neuroscience Annual Meeting/Abstract, (Aug. 27, 2004).
Sugiura et al, "The involvement of skeletal muscle in neurodegeneration in jSOD1 mice," Society of Neuroscience Annual Meeting/Abstract, (Aug. 27, 2004).
Szabo A et al, "Kennedy syndrome-bulbo-spinal muscular atrophy," Ideggyogy Sz, vol. 55 (No. 9-10), p. 323-9, (Sep. 20, 2002).
Tanaka F, et al, Somatic mosaicism of expanded CAG trinucleotide repeat in spinal and bulbar muscular atrophy (SBMA). Nippon Rinsho, vol. 57, p. 862-868, (Apr. 1999).
Tanaka, et al, "Tissue-specific somatic mosaicism in spinal and bulbar muscular atrophy is dependent on CAG-repeat length and androgen receptor-gene expression level," American Journal of Human Genetics, vol. 65, p. 966-973, (Oct. 1999).
Tuschl et al, "Small interfering RNAs: a revolutionary tool for the analysis of gene function and gene therapy," Mol. Interv. vol. 2 (No. 3), p. 158-167, (Jun. 2002).
Walker et al, "Carbenoxoline increases hepatic insulin sensitivity in man: a novel role for 11-oxosteroid reductase in enhancing glucocorticoid receptor activation," J. Clin Endorinol Metab, vol. 80 (No. 11), p. 3155-3159, (Nov. 1995).
Watanbe et al, "Mitotic and meiotic stability of the CAG repeat in the X-linked spinal and bulbar muscular atrophy gene," Clinical Genetics, vol. 50, (No. 3), p. 133-137, (1996).

* cited by examiner

*Primary Examiner*—Robert M. Kelly
*Assistant Examiner*—Kelaginamane T. Hiriyanna
(74) *Attorney, Agent, or Firm*—Price, Heneveld, Cooper, DeWitt & Litton, LLP

(57) ABSTRACT

The present invention describes a transgenic mouse susceptible to neuromuscular disease. The present invention also includes methods for treatment of neuromuscular diseases by interfering with activity between androgen and androgen receptors exclusively in the muscle fibers.

4 Claims, No Drawings

SEQUENCE LISTING

<160> NUMBER OF SEQ ID NOS: 4

<210> SEQ ID NO 1
<211> LENGTH: 6467
<212> TYPE: DNA
<213> ORGANISM: Artificial
<220> FEATURE:
<223> OTHER INFORMATION: Sources of genetic material are: homo sapiens and rat

<400> SEQUENCE: 1

-continued

```
ggtaccgggc cccccctcga ggtcgacggt atcgataagc tttctgtaag gaaaggtaag      60
agttgaactg agcaagagtt ttgaaaaata gtgacaatcc cattctcctt tggaatgcgc     120
acaaatattg aggtatccag tgaacggcag caaatttcct accttcaagg cccaaatgta     180
agctagtccc cttacgttac atgcagctca tttgctaagt ggttttttc tagtatctcc      240 actactcgct gacacaggag gacacaggat gttaaaaagg aaatacagtt ctgtcaatta     300
ttcacttact ctccaaaata cttggaagaa ctaaatatgg aaccatagga gactttatcc     360
tcaccgcata gtccctatac tagtcaaact cctatttttt taattgatca ttttttaggaa    420 ggtagcattt tattcactag aacattttg ttaatacttg tttattttg ggatgaactg       480 ccatgatgtg ggctacagag gagggtcgca tatgcttcca tccccttttt agagaatcca    540
cacctgtccc agttgctggg ttccactacc aaaagtgaat tgcaactatt ttaggagcac    600
ttaagcacat ccgaaaaatg agtgattctg ttctggccca caccatcca ctgatgtacc     660 cccttaaagc atgtccctga gttcatcaca gaagactgct cctcctgtgc cctccacaag   720
gttagaactg tccttgtctt agggaaaaag gagagagaga gagagagaga gagagagaga   780
gagagagaga gagagagaga gagagggaca ggcaccaact gggtaacctc tgctgacccc   840
cactctactt taccataagt agctccaaat ccttctagaa atctgaaag gcatagcccc    900 atatatcagt gatataaata gaacctgcag caggctctgg taaatgatga ctacaaggtg    960
gactgggagg cagcccggcc ttggcaggca tcatcctcta aatataaaga tgagtttgtt  1020
cagcctttgc agaaggaaaa actgccaccc atcctagagt gccgcgtcct tgtcccccca  1080
ccccctccaa tttattggga ggaaggacca gctaagcctc atctaggaag agcccctcac  1140
ccatctccac ctccactcca ggtctagcca gtcctgggtt gtgacccttg tctttcagcc  1200
ccaggagagg gacacacata gtgccaccaa agaggctggg ggagggcctc agcccaccaa  1260
aacctggggc cagtgcgtcc tacaggaggg gaaccctcac cccttcaatc cctttaggag  1320
acccaagggc gctgcgcgtc cctgaggcgg acagctccgt gtgctcaggc tttgcgcctg  1380
acaggcctat ccccgggagc ccccgcgcct cctccccggc gctccgccct cgcctccccc  1440
cgccagttgt ctatcctgcg acagctgcgc gccctccggc cgccggtggc cctctgtgcg  1500
gtgggggaag gggtcgacgt ggctcagctt tttggattca gggagctcgg gggtgggaag  1560
agagaaatgg agttccaggg gcgtaaagga gagggagttc gccttccttc ccttcctgag  1620
actcaggagt gactgcttct ccaatcctcc caagcccacc actccacacg actccctctt  1680
cccggtagtc gcaagtggga gtttggggat ctgagcaaag aacccgaaga ggagttgaaa  1740
tattggaagt cagcagtcag gcaccttccc gagcgcccag ggcgctcaga gtggacatgg  1800
ttggggaggc ctttgggaca ggtgcggttc ccggagcgca ggcgcacaca tgcacccacc  1860
ggcgaacgcg gtgaccctcg ccccacccca tcccctccgg cgggcaactg ggtcgggtca  1920
ggaggggcaa acccgctagg gagacactcc atatacggcc cggcccgcgt tacctgggac  1980
cgggccaacc cgctccttct ttggtcaacg caggggaccc gggcggggc ccaggccgcg   2040 aaccggccga gggaggggc tctagtgccc aacacccaaa tatggctcga gaagggcagc  2100
gacattcctg cggggtggcg cggagggaat gcccgcgggc tatataaaac ctgagcagag  2160
ggacaagcgg ccaccgcagc ggacagcgcc aagtgaagcc tcgcttcccc tccgcggcga  2220
ccagggcccg agccgagagt agcagttgta gctaccgcc caggtagggc aggagttggg   2280
aggggacagg gggacagggc actaccgagg ggaacctgaa ggactccggg gcagaaccca  2340
```

-continued

```
gtcggttcac ctggtcagcc ccaggcctgc gccctgagcg ctgtgcctcg tctccggagc    2400
cacacgcgct ttcaagcttt ttggcgtgta atacaaaatg acattcctag gctcacctca    2460
caggagcttg aaagaagaac ccaaagatat ttaagggaca gtttggcaag gtttttagag    2520
gaaactactt ggacagtaat taatgctcct gttaattggt ataactcttt acaagattac    2580
tactctactt tgtctcccat taggcctaca atggtgagac aagtagccaa cagggaaggg    2640
ttgcaaatat catttgggca cacctatgat aatattgatg aagcagacag tattcagcaa    2700
gtaactgaga ggtgggaagc tcaaagccaa agtcctaatg tgcagtcagg tgaatttatt    2760
gaaaaatttg aggctcctgg tggtgcaaat caaagaactg ctcctcagtg gatgttgcct    2820
ttacttctag gcctgtacgg aagtgttact tctgctctaa accggatcga tccctcgagt    2880
ctagagcggc cgcgcggccg ctctagaact agtggatccg aattcggtgg aagctagaga    2940
caagctaaag gatggaggtg cagttagggc tgggaagggt ctacccacgg cccccgtcca    3000
agacctatcg aggagcgttc cagaatctgt tccagagcgt gcgcgaagcg atccagaacc    3060
cgggccccag gcaccctgag gccgctagca tagcacctcc cggtgcctgt ttacagcagc    3120
ggcaggagac tagcccccgg cggcggcggc ggcagcagca ccctgaggat ggctctcctc    3180
aagcccacat cagaggcacc acaggctacc tggccctgga ggaggaacag cagccttcac    3240
agcagcagtc agcctccgag ggccaccctg agagcggctg cctccggag cctggagctg    3300 ccacggctcc tggcaagggg ctgccgcagc agccaccagc tcctccagat caggatgact    3360
cagctgcccc atccacgttg tccctactgg gccccacttt cccaggctta agcagctgct    3420
ccgcagacat taaagacatc ctgagcgagg ccggcaccat gcaacttctt gtaatatccg    3480
aaggcagcag cagcgtgaga gcaagggagg ccactgggc tccctcttcc tccaaggata    3540
gttacctagg gggcaattcg accatatctg acagtgccaa ggagttgtgt aaagcagtgt    3600
ctgtgtccat ggggttgggt gtggaagcac tggaacatct gagtccaggg gagcagcttc    3660
ggggcgactg catgtacgcg tcgctcctgg gaggtccacc cgccgtgcgt cccactcctt    3720
gtgcgcctct ggccgaatgc aaaggtcttt ccctggacga aggcccgggc aaaggcactg    3780
aagagactgc tgagtattcc tctttcaagg gaggttacgc caaagggttg aaggtgaga    3840 gtctgggctg ctctggcagc agtgaagcag gtagctctgg gacacttgag atcccgtcct    3900
cactgtctct gtataagtct ggagcagtag acgaggcagc agcataccag aatcgcgact    3960
actacaactt tccgctcgct ctgtccgggc cgccgcaccc cccgcccct acccatccac    4020 acgcccgcat caagctggag aacccgtcgg actacggcag cgcctgggct gcggcggcag    4080
cgcaatgccg ctatgggac ttggctagcc tacatggagg gagtgtagcc ggacccagca    4140
ctggatcgcc cccagccacc gcctcttctt cctggcatac tctcttcaca gctgaagaag    4200
gccaattata tgggccagga ggcgggggcg gcagcagtag cccaagcgat gctgggcctg    4260
tagcccccta tggctacact cggccccctc aggggctggc aagccaggag ggtgacttct    4320
ctgcctctga agtgtggtat cctggtggag ttgtgaacag agtcccctat cccagtccca    4380
gttgtgttaa aagtgaaatg ggaccttgga tggagaacta ctccggacct tatgggggaca    4440 tgcgtttgga cagtaccagg gaccacgttt tacccatcga ctattacttc ccaccccaga    4500
agacctgcct gatctgtgga gatgaagctt ctggttgtca ctacgagct ctcacttgtg    4560 gcagctgcaa ggtcttcttc aaaagagctg cggaagggaa acagaagtat ctatgtgcca    4620
gcagaaatga ttgcaccatt gataaatttc ggaggaaaaa ttgtccatcg tgtcgtctcc    4680
ggaaatgtta tgaagcaggg atgactctgg gagctcgtaa gctgaagaaa cttggaaatc    4740
```

-continued

| | |
|---|---|
| tcaaactaca ggaagaagga gaaaactcca gtgctggtag ccccactgag gacccatccc | 4800 |
| agaagatgac tgtatcacac attgaaggct atgaatgtca acctatcttt cttaatgtcc | 4860 |
| tggaagccat tgagccagga gtggtgtgtg ccggacatga caacaaccag cctgattcct | 4920 |
| ttgctgcctt gttatctagt ctcaacgagc ttggcgagag acagcttgta catgtggtca | 4980 |
| agtgggccaa ggccttgcct ggcttccgca acttgcatgt ggatgaccag atggcagtca | 5040 |
| ttcagtattc ctggatggga ctgatggtat ttgccatggg ttggcggtcc ttcactaatg | 5100 |
| tcaactctag gatgctctac tttgcacctg acctggtttt caatgagtat cgcatgcaca | 5160 |
| agtctcgaat gtacagccag tgcgtgagga tgaggcacct ttctcaagag tttggatggc | 5220 |
| tccagataac cccccaggaa ttcctgtgca tgaaagcact gctactcttc agcattattc | 5280 |
| cagtggatgg gctgaaaaat caaaaattct ttgatgaact tcgaatgaac tacatcaagg | 5340 |
| aacttgatcg catcattgca tgcaaaagaa aaaatcccac atcctgctca aggcgcttct | 5400 |
| accagctcac caagctcctg gattctgtgc agcctattgc aagagagctg catcaattca | 5460 |
| cttttgacct gctaatcaag tcccatatgg tgagcgtgga cttcctgaa atgatggcag | 5520 |
| agatcatctc tgtgcaagtg cccaagatcc tttctgggaa agtcaagccc atctatttcc | 5580 |
| acacacagtg aagatttgga aaccctaata cccaaaccca ccttgttccc ttttcagatg | 5640 |
| tcttctgcct gttatataac tctgcactac ttctctggca tgggccttgg gggaaattcc | 5700 |
| tctactgatg tacagtctgt catgaacatg ttccccaagt tctatttcct ggcttttcc | 5760 |
| ttctttcttt ttcttcttct ctgcctcttt taccctccca tggcacattt tgaatccgct | 5820 |
| gcgtgttgtg gctcctgcct gtgttttgag ttttgttgta tttcttcaag tctgtgatga | 5880 |
| tcttcttgtg gcccagtgtc aactgtgctt gtttatagca ctgtgctgtg tgccaaccaa | 5940 |
| gcaaatgttt actcaccta tgccatggca gtttagaga ctataagta tcttgggaag | 6000 |
| aaacaaacag agagagtaaa aaaaccgaat tcccggtacc gcggccgcgc accgcggcgc | 6060 |
| cttaattaat agatccagac atgataagat acattgatga gtttggacaa accacaacta | 6120 |
| gaatgcagtg aaaaaaatgc tttatttgtg aaatttgtga tgctattgct ttatttgtaa | 6180 |
| ccattataag ctgcaataaa caagttaaca acaacaattg cattcatttt atgtttcagg | 6240 |
| ttcaggggga ggtgtgggag gttttttcgg atccagacat gataagatac attgatgagt | 6300 |
| ttggacaaac cacaactaga atgcagtgaa aaaatgctt tatttgtgaa atttgtgatg | 6360 |
| ctattgcttt atttgtaacc attataagct gcaataaaca agttaacaac aacaattgca | 6420 |
| ttcattttat gtttcaggtt caggggagg tgtgggaggt tttttcg | 6467 |

<210> SEQ ID NO 2
<211> LENGTH: 3146
<212> TYPE: DNA
<213> ORGANISM: rat

<400> SEQUENCE: 2

| | |
|---|---|
| gcggccgctc tagaactagt ggatccgaat tcggtggaag ctagagacaa gctaaaggat | 60 |
| ggaggtgcag ttagggctgg gaagggtcta cccacggccc ccgtccaaga cctatcgagg | 120 |
| agcgttccag aatctgttcc agagcgtgcg cgaagcgatc cagaacccgg gcccaggca | 180 |
| ccctgaggcc gctagcatag caccctcccgg tgcctgttta cagcagcggc aggagactag | 240 |
| cccccgcgg cggcgcggc agcagcaccc tgaggatggc tctcctcaag cccacatcag | 300 |
| aggcaccaca ggctacctgg ccctggagga ggaacagcag ccttcacagc agcagtcagc | 360 |

-continued

```
ctccgagggc acccctgaga gcggctgcct cccggagcct ggagctgcca cggctcctgg    420 caagggctg ccgcagcagc caccagctcc tccagatcag gatgactcag ctgccccatc     480
cacgttgtcc ctactgggcc ccactttccc aggcttaagc agctgctccg cagacattaa    540
agacatcctg agcgaggccg gcaccatgca acttcttgta atatccgaag gcagcagcag    600
cgtgagagca agggaggcca ctggggctcc ctcttcctcc aaggatagtt acctagggg     660 caattcgacc atatctgaca gtgccaagga gttgtgtaaa gcagtgtctg tgtccatggg    720
gttgggtgtg gaagcactgg aacatctgag tccaggggag cagcttcggg gcgactgcat    780
gtacgcgtcg ctcctgggag gtccacccgc cgtgcgtccc actccttgtg cgcctctggc    840
cgaatgcaaa ggtctttccc tggacgaagg cccgggcaaa ggcactgaag agactgctga    900
gtattcctct ttcaagggag gttacgccaa agggttggaa ggtgagagtc tgggctgctc    960
tggcagcagt gaagcaggta gctctgggac acttgagatc ccgtcctcac tgtctctgta   1020
taagtctgga gcagtagacg aggcagcagc ataccagaat cgcgactact acaacttccc   1080
gctcgctctg tccgggccgc cgcaccccc gccccctacc catccacacg cccgcatcaa    1140
gctggagaac ccgtcggact acggcagcgc ctgggctgcg gcggcagcgc aatgccgcta   1200
tggggacttg gctagcctac atggagggag tgtagccgga cccagcactg gatcgccccc    1260
agccaccgcc tcttcttcct ggcatactct cttcacagct gaagaaggcc aattatatgg    1320
gccaggaggc gggggcggca gcagtagccc aagcgatgct gggcctgtag cccctatgg    1380 ctacactcgg ccccctcagg ggctggcaag ccaggaggt gacttctctg cctctgaagt     1440
gtggtatcct ggtggagttg tgaacagagt cccctatccc agtccagtt gtgttaaaag     1500 tgaaatggga ccttggatgg agaactactc cggaccttat ggggacatgc gtttggacag    1560
taccagggac cacgttttac ccatcgacta ttacttccca ccccagaaga cctgcctgat    1620
ctgtggagat gaagcttctg gttgtcacta cggagctctc acttgtggca gctgcaaggt    1680
cttcttcaaa agagctgcgg aagggaaaca gaagtatcta tgtgccagca gaaatgattg    1740
caccattgat aaatttcgga ggaaaaattg tccatcgtgt cgtctccgga atgttatga    1800 agcagggatg actctgggag ctcgtaagct gaagaaactt ggaaatctca aactacagga    1860
agaaggagaa aactccagtg ctggtagccc cactgaggac ccatcccaga agatgactgt    1920
atcacacatt gaaggctatg aatgtcaacc tatctttctt aatgtcctgg aagccattga    1980
gccaggagtg gtgtgtgccg gacatgacaa caaccagcct gattcctttg ctgccttgtt    2040
atctagtctc aacgagcttg gcgagagaca gcttgtacat gtggtcaagt gggccaaggc    2100
cttgcctggc ttccgcaact tgcatgtgga tgaccagatg gcagtcattc agtattcctg    2160
gatgggactg atggtatttg ccatggggttg gcggtccttc actaatgtca actctaggat    2220
gctctacttt gcacctgacc tggttttcaa tgagtatcgc atgcacaagt ctcgaatgta    2280
cagccagtgc gtgaggatga ggcacctttc tcaagagttt ggatggctcc agataacccc    2340
ccaggaattc ctgtgcatga aagcactgct actcttcagc attattccag tggatgggct    2400
gaaaaatcaa aaattctttg atgaacttcg aatgaactac atcaaggaac ttgatcgcat    2460
cattgcatgc aaaagaaaaa atcccacatc ctgctcaagg cgcttctacc agctcaccaa    2520
gctcctggat tctgtgcagc ctattgcaag agagctgcat caattcactt ttgacctgct    2580
aatcaagtcc catatggtga gcgtggactt tcctgaaatg atggcagaga tcatctctgt    2640
gcaagtgccc aagatccttt ctgggaaagt caagcccatc tatttccaca cacagtgaag    2700
atttggaaac cctaataccc aaacccacct tgttcccttt tcagatgtct tctgcctgtt    2760
```

-continued

| | | | | |
|---|---|---|---|---|
| atataactct | gcactacttc | tctggcatgg | gccttggggg | aaattcctct actgatgtac | 2820 |
| agtctgtcat | gaacatgttc | cccaagttct | atttcctggg | cttttccttc tttcttttc | 2880 |
| ttcttctctg | cctctttttac | cctcccatgg | cacattttga | atccgctgcg tgttgtggct | 2940 |
| cctgcctgtg | ttttgagttt | tgttgtattt | cttcaagtct | gtgatgatct tcttgtggcc | 3000 |
| cagtgtcaac | tgtgcttgtt | tatagcactg | tgctgtgtgc | caaccaagca aatgtttact | 3060 |
| caccttatgc | catggcaagt | ttagagagct | ataagtatct | tgggaagaaa caaacagaga | 3120 |
| gagtaaaaaa | accgaattcc | cggtac | | | 3146 |

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
agtagccaac agggaagggt                                                     20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cagattctgg aacgctcctc                                                     20

TRANSGENIC MOUSE MODEL AND METHODS FOR TREATMENT OF NEURO MUSCULAR DISEASE BY INTERFERING WITH ANDROGEN-ANDROGEN RECEPTOR INTERACTION IN SKELETAL MUSCLES

CROSS-REFERENCE TO RELATED APPLICATION

This application claims the benefit under 35 U.S.C. § 119(e) of U.S. Provisional Application No. 60/711,333, entitled Transgenic Mouse Model and Methods for Treatment of Neuro Muscular Disease by Interfering with Androgen-Androgen Receptor Interaction in Skeletal Muscles, filed on Aug. 25, 2005, the entire disclosure of which is hereby incorporated herein by reference.

FIELD OF THE INVENTION

This invention relates to a transgenic mouse model and methods of treating neuromuscular disorders, such as spinal bulbar muscular atrophy or amyotrophic lateral sclerosis.

BACKGROUND OF THE INVENTION

Spinal bulbar muscular atrophy (SBMA), also known as Kennedy's disease, Kennedy's syndrome, bulbospinal muscular atrophy, and X-linked recessive spinal bulbar muscular atrophy, is a slowly progressive neuromuscular disorder that strikes people, primarily men, in late adulthood. It is characterized by progressive muscle weakness including bulbar signs, facial fasciculations, dysphagia, numbness, reduced reflexes, tremor, reduced androgen sensitivity, severe cramps, hypothalamic defect, problems with speech and swallowing, as well as lower motor and primary sensory neuropathy. With this disease, muscle weakness and wasting is generally noted in the lower body and eventually spreads to the upper extremities over time.

SBMA is known to be caused by a genetic mutation in the androgen receptor gene on the X chromosome in humans. SBMA is recessive in nature, in that only males tend to develop SBMA, and not females. Females have two X chromosomes whereas males have only a single X chromosome. Thus, female carriers of SBMA have two copies of the androgen receptor gene—one mutated copy and one good copy. The presence of a normal androgen receptor gene on one X chromosome in female carriers may protect such females from developing full blown symptoms of the disease. Alternatively, females also have a much lower level of androgens than males and this low level of androgens is likely to be a critical factor for why females tend to not show SBMA, given that even females with two bad copies of the androgen receptor gene also show little or no symptoms of SBMA. On other hand, each male born from a carrier female (one good copy and one bad copy of the androgen receptor gene) has a fifty percent chance of inheriting the gene and developing the disease. This high percentage is based on the fact that males receive their only X chromosome from their mother and if this X chromosome has the mutated gene, they will one day develop the symptoms of SBMA.

The X-linked genetic mutation is an expansion of a CAG trinucleotide repeat in the coding region of the androgen receptor (AR) gene. The CAG trinucleotide is repeated up to 34 times in a normal AR gene. Any amount greater than 35 CAGs constitutes an expansion of the trinucleotide repeat. The abnormally expanded CAG trinucleotide repeat changes the structure of the AR protein produced by the AR gene. The resulting AR protein has a longer string of glutamines (polyglutamine repeats), which if substantial enough, can lead to SBMA in adulthood. Recent evidence based on animal studies suggests that androgens such as testosterone, dehydroepiandrosterone, androstenedione, androstanediol, androsterone, dihydrotestosterone and other steroid hormones can trigger the symptoms of SBMA when they interact with androgen receptors. How polyglutamine tract expansion leads to neurodegeneration in SBMA and other polyglutamine tract diseases is still unknown.

SBMA is widely presumed to be caused by the death of motoneurons, eventually leading to the atrophy of muscles. It is currently believed that the abnormally expanded CAG trinucleotide repeats, and the resulting changes in the structure of the AR protein, disrupt the normal function of motoneurons in the brain and spinal cord leading to SBMA. It is currently held that as these motoneurons gradually die, weakness, wasting and general deterioration of muscles develop as secondary consequences of the motoneuron degradation.

Although SBMA has a known genetic cause, there is currently no cure for SBMA sufferers. Patients afflicted by this disease must resort to physical therapy and speech/swallowing therapy to help control symptoms. Several efforts to compensate for loss of normal androgen receptor function through androgen replacement therapy have failed. Current research focuses on unraveling the mutant receptor's toxic gain of function (when a protein becomes toxic because of a gene flaw) and designing treatments to inhibit that function. Currently, all administered treatments are designed to mitigate the effects of failing muscles and curb the discomfort of patients through pain management.

At the present time, there are no known spontaneous animal mutations with sufficient similarities to SBMA to be useful as experimental models. In order to yield useful information on etiology or treatment of SBMA, appropriate animal models must be developed. With appropriate animal models, researchers can develop methods of treatment that effectively combat the symptoms of SBMA. SBMA animal models also will allow researchers to develop treatments that terminate the progression of the disease and possibly reverse symptoms.

SUMMARY OF THE INVENTION

An aspect of the present invention is to provide a transgenic mouse model whose genome comprises an androgen receptor transgene. The androgen receptor in the model expresses the androgen receptor transgene exclusively in muscle fibers resulting in up-regulated levels of androgen receptor protein.

Another aspect of the present invention includes providing a method for treating a neuromuscular disorder by injecting anti-androgens directly into muscle cells to interfere with androgen action. In another aspect of the present invention, the anti-androgen cannot enter into the central nervous system, for example, the anti-androgen lacks the ability to traverse the blood brain barrier.

Yet another aspect of the present invention includes providing a method for treating a neuromuscular disorder by inhibiting with a reductase inhibitor the conversion of testosterone into 5alpha dihydrotestosterone in muscle cells.

Yet another embodiment of the present invention includes a method for treating a neuromuscular disorder by increasing conversion of testosterone into an ineffective androgen (e.g.

5beta dihydrotestosterone) in muscle tissue, thus inhibiting activation of androgen receptors in muscle tissue.

DETAILED DESCRIPTION OF THE PREFERRED EMBODIMENTS

The preferred embodiments of the present invention may be understood more readily by reference to the following detailed description of the preferred embodiments the Example, and the Sequence Listing included hereafter.

The Sequence Listing filed with this application contained on a compact disk titled "CFR," with file title "MIC37 PP327 Sequence Listing.ST25.txt" is incorporated-by-reference. This compact disc was created on Aug. 22, 2006, and is 14.0 kilobytes.

One embodiment of the present invention provides an improved model for effectively exploring treatments for neuromuscular disorders, such as SBMA. Specifically, an animal model has been developed for studying spinal bulbar muscular atrophy, and for evaluating the therapeutic efficacy of proposed SBMA treatments. The animal model of the present invention is a transgenic mouse that has (1) a heterologous copy of an androgen receptor (AR) gene in the DNA of mouse cells, (2) a promoter from the human skeletal actin (hsa) gene which drives expression of the AR gene exclusively in skeletal muscle fibers without affecting expression of the endogenous AR gene in other types of cells that ordinarily have the AR protein (including but not limited to motoneurons, brains cells, fibroblasts, and prostate cells). The exclusive upregulation of AR protein only in skeletal muscle fibers (due to expression of the AR transgene only in this cell type) allows for the evaluation of new and innovative SBMA therapies directed solely at the androgen-AR protein interaction in the muscle fibers.

The transgenic mice described herein were generated by introduction of a specific transgene (termed the hsaAR transgene hereafter) into a pronucleus of early stage (0.5 days post coitum) mouse zygotes via microinjection. Microinjected zygotes were then introduced into oviducts of pseudopregnant mouse dams, who were allowed to come to term. The presence of said transgene in the progeny of these pseudopregnant dams was detected by polymerase chain reaction (PCR) of tissue using primers (5' AGTAGCCAA-CAGGGAAGGGT 3' (SEQ ID NO. 3) and 5' CAGATTCTG-GAACGCTCCTC 3' (SEQ ID NO. 4) that span the recombinant regions of the transgene and thus whose combination is unique to the transgene and do not detect genes in the genome of the background strain. Progeny in which the transgene was detected were bred with wild type C57/B16J mice to generate founding lines. These founding lines were then analyzed for neuromuscular phenotype and transgene expression.

Said transgene consists of recombinant DNA which includes an androgen receptor coding sequence in a muscle fiber specific expression cassette. The nucleotide sequence of the hsaAR transgene is shown as SEQ ID NO. 1. The transgene includes four essential elements. First, the transgene includes the promoter region of the ACTA1 gene (also known as skeletal actin, alpha 1 actin; see SEQ ID NO. 1, bases 1-2507) that is a base pair fragment of this gene upstream of the transcription initiation site cloned from human genomic DNA. This element confers the specificity of expression of the transgene. Second, the transgene includes an intron that is a base pair fragment from the first intron of the VP1 gene of simian virus 40 (SV40; see SEQ ID NO. 1, bases 2508-2885). This element allows for the efficient expression of the coding sequence. Third, the transgene includes the coding sequence of exons of the AR gene (also known as androgen receptor, tfm, Rat Genome Database locus: 2147; see SEQ ID NO. 1, bases 2894-6039; and SEQ ID NO. 2) that is a base pair fragment of the complementary DNA (cDNA) to the rat androgen receptor messenger RNA (mRNA), including the entire coding sequence for the wild type AR protein. This element confers the ability to produce AR protein corresponding to the transgene. Fourth, the transgene includes two repeats of the polyadenylation sequence of the VP1 gene of simian virus 40 (see SEQ ID NO. 1, bases 6072-6467) that is a base pair fragment. This element limits the length of transcripts arising from the transgene and increases the stability of these transcripts.

The transgene also includes two additional elements that are located at either end of the coding sequence of exons of the AR gene. The first of these two elements (see SEQ ID NO. 1, bases 2886-2893) is a NotI restriction enzyme recognition site. The second element (see SEQ ID NO. 1, bases 6040-6071) is a linkage that includes a NotI restriction enzyme recognition site.

The essential elements of the novel transgene, with the exception of the coding sequence of exons of the AR gene, collectively consist of a muscle fiber specific expression cassette, as they might be used together to generate many transgenes, each with the ability to express a different protein of interest in muscle fiber. Different clones of promoters or enhancers from muscle fiber specific genes might be used, or artificial constructs consisting of the regulatory elements found therein might also be used to create transgenes with a similar cellular specificity and biological activity. Similarly, different AR clones or mutants might be used with the same net effect. The hsaAR transgene was assembled using recombinant DNA technology, but might be assembled by other means with the same net effect.

Using the transgenic mouse model of the present invention, the inventors have concluded that the interaction of androgens with the androgen receptor in the muscle fibers initiates the symptoms of SBMA. Thus, the present invention also includes using various therapies to interfere with the interaction between androgens with androgen receptors in the muscle, thereby providing an effective and ground-breaking treatment for the disease.

The inventors have developed several treatments for SBMA, amyotrophic lateral sclerosis (ALS), or other neuromuscular disorders, that target androgen-androgen receptor interaction in muscle cells. The first treatment involves the delivery of pharmacological anti-androgens to muscle in an effective amount such that these anti-androgens will interfere with activation of the androgen receptor by androgens. Anti-androgens, such as flutamide (or its active metabolite, hydroxyflutamide) or cyproterone acetate, interfere with androgen receptor activity by binding to and blocking activation of the androgen receptor by androgens. The local muscle aspect of this treatment allows the administrator to provide effective relief for SBMA without affecting the endogenous androgen production from the body and avoids adverse affects of androgen (or lack thereof) on the brain. The anti-androgens of the present invention can be administered through various channels. One such delivery method includes injecting anti-androgens directly into muscles.

Another delivery method of the present invention comprises the use of gene therapy to produce anti androgens locally in the muscles, or to interfere with androgen receptor activation in muscles. For example, production of short interfering RNAs to reduce mRNA for the androgen receptor, and hence reducing androgen receptor protein in muscles. Another approach would be to use gene therapy to cause muscles to produce enzymes, such as 5beta reductase, locally in muscles to convert potent androgens such as testosterone into ineffective androgens such as 5beta dihydrotestosterone, thus decreasing activation of androgen receptors in muscle.

Yet another method of delivering an effective amount of anti-androgen to the muscle fibers is the use of anti-androgenic compounds that have a greater affinity for muscle cells than other cell types. Further, the present invention includes anti-androgenic compounds that do not have the ability to traverse the blood brain barrier; such compounds would result in local interference of androgen to androgen receptor interaction without affecting endogenous androgen production or the effects of androgen on the brain.

Another treatment method of SBMA, ALS, or other neuromuscular disorders, includes altering the production of androgen metabolites in muscle tissue. Specifically, enzymes such as 5alpha-reductases are known to convert testosterone into 5alpha dihydrotestosterone. 5alpha dihydrotestosterone is a more effective androgen than testosterone in that it binds more tenaciously to androgen receptors. Because 5alpha dihydrotestosterone has a greater affinity for androgen receptors, 5alpha reductase serves to amplify androgen activity. By administering known reductase inhibitors, such as finasteride, into the muscle tissue, the effects of the 5alpha reductase would be effectively inhibited in the muscle tissue. Reductase inhibitors work by offering an alternative substrate for 5alpha reductase to act on which in turns prevents 5alpha reductase from acting on testosterone. Through this action, production of the more potent 5alpha dihydrotestosterone is prevented. Thus, the amplified androgen activity is effectively terminated in the muscle tissue. Introduction of reductase inhibitors into the muscle fibers can be carried out by any one of the above described means for delivery of anti-androgens. The present method of inhibiting reductase activity is an effective treatment for neuromuscular disorders (e.g. SBMA or ALS) while not interfering with endogenous androgen production and its use in other non-muscle tissues.

Another inventive method of treatment for SBMA, ALS, or other neuromuscular disorders, includes increasing production of the enzyme 5beta reductase in muscle cells. 5beta reductase catalyzes the conversion of testosterone into 5beta hydrotestosterone. 5beta hydrotestosterone is a very ineffective androgen, representing a "degradation shunt" because it cannot be converted back to testosterone or any other variation of an effective androgen. Again, a local effective dosage of 5beta reductase, or any similarly behaving enzyme, in the muscle tissue would serve to shunt any testosterone molecules into ineffective androgens that cannot activate androgen receptors nor be converted back to effective androgens. Such a treatment would relieve symptoms of SBMA with little to no side effects of androgen withdrawal in other parts of the body. Introduction of such reductases in muscle cells can be carried out by any one of the above-described means for delivery of anti-androgens.

EXAMPLE

A Model for Studies of Spinal Bulbar Muscular Atrophy and Treatment

Transgenic mice prepared in the present invention exhibit a high mortality rate perinatally. On the other hand, transgenic females do not show this same mortality. Loss of transgenic males before or just after birth may be caused by testosterone since only developing transgenic males and not transgenic females die. The testes of male mice produce androgen and testosterone during embryonic and perinatal development. Since females do not have testes, they do not have the androgens produced by this organ. It is likely that the androgens produced by testes in combination with an abnormally high number of androgen receptors in muscle fibers (caused by expression of the transgene) becomes toxic to transgenic males and kills them. Normal males do not have a high mortality rate in utero and/or at birth because they have many fewer androgen receptors in their muscle fibers than transgenic males.

Male carriers that survive birth appear healthy until they reach puberty. During puberty the males exhibit increased secretions of testosterone. With the increased androgen in their systems, these mice display the symptoms of SBMA due to the activation by androgens of a high number of androgen receptors in their muscle fibers.

While transgenic females survive in utero, and appear healthy after birth, females that carry the transgene will also develop SBMA if they are treated with androgen. Being that the transgene in these mice is solely expressed in the muscle cells, it is evident that the symptoms of SBMA are triggered by androgen activating its receptor in muscle cells which then affect other tissues in the body. The effect of androgen treatment on carrier females is however reversible. If the androgen treatment is terminated, such carrier females will recover from SBMA, with an apparently complete reversal of SBMA symptoms. This indicates that blocking the effects on androgens in the muscles of males that already suffer from SBMA will relieve SBMA symptoms.

The above description is considered that of the preferred embodiments only. Modifications of the invention will occur to those skilled in the art and to those who make or use the invention. Therefore, it is understood that the embodiments shown above are merely for illustrative purposes and not intended to limit the scope of the invention, which is defined by the following claims as interpreted according to the principles of patent law, including the doctrine of equivalents.

What is claimed is:

1. A method for treating spinal bulbar muscular atrophy (SBMA) comprising; injecting an anti-androgen directly into a muscle cell affected by SBMA, which anti-androgen is selected from the group consisting of flutamide, hydroxyflutamide and cyproterone acetate; wherein the affects of SBMA in the muscle cell are reduced.

2. The method of claim 1 wherein the anti-androgen is flutamide.

3. The method of claim 1 wherein the anti-androgen is hydroxyflutamide.

4. The method of claim 1 wherein the anti-androgen is cyproterone acetate.

* * * * *

UNITED STATES PATENT AND TRADEMARK OFFICE
CERTIFICATE OF CORRECTION

PATENT NO.        : 7,655,700 B2                                                      Page 1 of 1
APPLICATION NO.   : 11/509455
DATED             : February 2, 2010
INVENTOR(S)       : Cynthia Jordan et al.

It is certified that error appears in the above-identified patent and that said Letters Patent is hereby corrected as shown below:

Column 1
Lines 53-54 "on other hand" should be -- on the other hand --.

Column 3
Line 9 "embodiments the" should be -- embodiments, the --.

Column 4
Line 56 "affects" should be -- effects --;
Line 61 "anti androgens" should be -- anti-androgens --.

Column 15, claim 1
Line 42 "affects" should be -- effects --.

Signed and Sealed this
Twenty-first Day of June, 2011

David J. Kappos
*Director of the United States Patent and Trademark Office*